(12) United States Patent
Lane (10) Patent No.: US 10,953,124 B2
(45) Date of Patent: Mar. 23, 2021

(54) VOLATILE COMPOSITION DISPENSER

(71) Applicant: The Procter & Gamble Company, Cincinnati, OH (US)

(72) Inventor: Richard Lee Lane, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 313 days.

(21) Appl. No.: 15/939,344

(22) Filed: Mar. 29, 2018

(65) Prior Publication Data

US 2019/0298877 A1 Oct. 3, 2019

(51) Int. Cl.
*A61L 9/12* (2006.01)

(52) U.S. Cl.
CPC .................... *A61L 9/122* (2013.01)

(58) Field of Classification Search
CPC ............ A61L 9/122; A61L 9/014; A61L 9/14
See application file for complete search history.

(56) References Cited

U.S. PATENT DOCUMENTS

| | | | | |
|---|---|---|---|---|
| 2,910,225 A * | 10/1959 | Whitling | ............... | F04D 25/084 261/24 |
| 4,676,721 A * | 6/1987 | Hardee | .................. | A61L 9/122 416/146 R |
| 5,383,765 A * | 1/1995 | Baxter | ...................... | A61L 9/12 261/84 |
| 5,564,900 A * | 10/1996 | McAuley | ............. | F04D 25/088 416/62 |
| 5,887,118 A * | 3/1999 | Huffman | ................ | A61M 15/00 361/679.32 |
| 5,947,686 A * | 9/1999 | Keyes | ................... | F04D 29/388 239/35 |
| 6,109,874 A * | 8/2000 | Steiner | .................. | F04D 25/084 416/229 R |
| 6,613,287 B1 * | 9/2003 | McElligott | .............. | A61L 9/042 239/57 |
| 6,764,656 B1 * | 7/2004 | Matulevich | ............... | A61L 9/12 422/124 |
| 7,037,074 B2 * | 5/2006 | Hoshino | ............... | F04D 25/088 416/132 A |
| 7,097,161 B2 * | 8/2006 | Liou | ......................... | A61L 9/03 261/142 |
| 7,661,929 B1 * | 2/2010 | McVay | ..................... | A61L 9/12 416/146 R |
| 8,025,481 B2 * | 9/2011 | Foxworth | ............. | F04D 29/005 416/62 |
| 8,043,569 B2 | 10/2011 | Tranzeat | | |
| 9,327,046 B2 | 5/2016 | Turner | | |

(Continued)

FOREIGN PATENT DOCUMENTS

GB 00175387 * 2/1922 ............. A61L 9/122

*Primary Examiner* — Regina M Yoo
(74) *Attorney, Agent, or Firm* — Abbey A. Lopez (57) ABSTRACT

A volatile composition dispenser and a method of volatilizing a liquid volatile composition is provided. The volatile composition dispenser includes a reservoir and a fan. The fan is disposed at least partially in the reservoir. The fan includes a motor, a hub rotatably connected to the motor about a rotation axis, a fan blade connected with the hub. The fan blade is movable relative to the hub about a pivot axis. The pivot axis is perpendicular or substantially perpendicular to the rotation axis. The at least one fan blade comprises an absorbent material.

15 Claims, 5 Drawing Sheets

(56) References Cited

U.S. PATENT DOCUMENTS

| | | | |
|---|---|---|---|
| 10,384,774 B2 * | 8/2019 | Vondrell | H02J 7/0042 |
| 2004/0141288 A1 * | 7/2004 | Franz | H05K 7/20727 |
| | | | 361/695 |
| 2008/0003104 A1 * | 1/2008 | Betlach | F24F 7/007 |
| | | | 416/62 |
| 2012/0224967 A1 * | 9/2012 | Radabaugh | F04D 29/705 |
| | | | 416/62 |
| 2013/0340190 A1 * | 12/2013 | Allen | A47L 25/00 |
| | | | 15/210.1 |

* cited by examiner

VOLATILE COMPOSITION DISPENSER

FIELD

The present disclosure is directed to a volatile composition dispenser, and, more particularly, is directed to a volatile composition dispenser comprising a reservoir and a fan having absorbent fan blades.

BACKGROUND

Various devices in the marketplace provide a non-energized, continuous emission of a liquid volatile composition (e.g. perfume or insect repellant) to the atmosphere, whereby such emission can plateau and taper off over time. Increasing the emission level of a liquid volatile composition over its emission level in a non-energized state has been attempted with energized air freshening devices that include diffusion assistance means, such as heating elements, piezoelectric elements, and/or motorized fans. The addition of such diffusion assistance means in a device may require a larger amount of liquid volatile composition and/or a larger device to accommodate the diffusion assistance means, and, in turn, higher manufacturing and product cost. Energized devices often include a delivery engine, such as a wick, membrane, gel, etc., that may limit the diffusion of certain types of volatile materials or comprises a porous substrate that may leak fluid when in certain orientations. Some energized devices can also suffer from emission plateaus or tapering. Thus, there remains a need for improved devices that dispense liquid volatile compositions into the atmosphere.

SUMMARY

Combinations:
A. A volatile composition dispenser comprising:
 a reservoir;
 a fan disposed at least partially in the reservoir, wherein the fan comprises a motor, a hub rotatably connected to the motor about a rotation axis, a fan blade connected with the hub, wherein the fan blade is movable relative to the hub about a pivot axis, wherein the pivot axis is perpendicular or substantially perpendicular to the rotation axis, wherein the at least one fan blade comprises an absorbent material.
B. The volatile composition dispenser according to Paragraph A further comprising a connector that joins the fan blade with the hub.
C. The volatile composition dispenser according to Paragraph A or Paragraph B, wherein the connector is selected from the group consisting of: hinge, clip, clamp, pin, fastener, snap, buckle, spring-loaded fastener, threaded fastener, hook-and-loop fastener, permanent or releasable adhesive, tape, and combinations thereof.
D. The volatile composition dispenser according to any of Paragraphs A-C, wherein the absorbent material is selected from the group consisting of: woven material, non-woven material, foam, or combinations thereof.
E. The volatile composition dispenser according to any of the Paragraphs A-D, wherein the fan comprises a plurality of fan blades connected with the hub.
F. The volatile composition dispenser according to any of Paragraphs A-E, wherein the fan blade is releasably connectable with the hub.
G. The volatile composition dispenser according to any of Paragraphs A-F, wherein the liquid volatile composition comprises a material selected from the group consisting of: a perfume, an insect repellant, a deodorizer, a malodor counteractant, and combinations thereof.
H. The volatile composition dispenser according to any of Paragraphs A-G, wherein the fan blade is configured such that when the motor is on, centrifugal force causes the fan blade to move from a closed configuration to an open configuration, wherein the angle between the closed configuration and the open configuration is about 90 degrees.
I. A kit comprising the volatile composition dispenser according to any of Paragraphs A-H and a container comprising a liquid volatile composition.
J. A method of dispensing a liquid volatile composition from a volatile composition dispenser, the volatile composition dispenser comprising a reservoir and a fan disposed at least partially in the reservoir, wherein the fan comprises a motor, a hub rotatably connected to the motor about a rotation axis, and at least one fan blade connected with the hub and movable about a pivot axis relative to the hub, wherein the at least one fan blade comprises a absorbent material, the method comprising the steps of:
 powering the motor of the fan;
 moving the at least one fan blade from a closed configuration to an open configuration;
 volatilizing a liquid volatile composition from the at least one fan blade;
 turning off the power to the motor; and
 returning the at least one fan blade from the open configuration to the closed configuration.
K. The method according to Paragraph J further comprising the steps of:
 Collecting liquid volatile composition in the reservoir; and
 absorbing the liquid volatile composition collected in the reservoir when the at least one fan blade is in the closed configuration.
L. The method according to Paragraph J or Paragraph K, wherein the at least one fan blade moves about 90 degrees from the closed configuration to the open configuration.
M. The method according to any of Paragraphs J-L, further comprising the step of applying a liquid volatile composition to the at least one fan blade.
N. The method according to any of Paragraphs J-M further comprising the step of removing the at least one fan blade from the hub and replacing the at least one fan blade with a new fan blade.

DETAILED DESCRIPTION

The present disclosure provides a volatile composition dispenser having a reservoir and a fan disposed at least partially in the reservoir for assisting with the volatilization of a liquid volatile composition. The fan is configured with a motor, a hub rotatably connected with the motor about a rotation axis, and one or more fan blades connected with the hub. The fan blades are designed to pivot relative to the hub about a pivot axis from a closed configuration to an open configuration. The pivot axis may be disposed approximately 90 degrees relative to the rotation axis. The fan blades may rotate from a substantially vertical, closed configuration to a substantially horizontal, open configuration. The fan blades may rotate about 90 degrees from the closed configuration to the open configuration. The fan blades also comprise an absorbent material to absorb a liquid volatile composition. Upon operation of the fan, the fan blades move from the closed configuration to the open configuration by way of the centrifugal force acting on the fan blades. The air flow generated by the rotating fan blades assists with the volatilization of a liquid volatile composition from the fan blades. When the motor is stopped, the fan blades return to a closed configuration. In the closed configuration, fluid accumulated or provided in the reservoir may be absorbed or reabsorbed by the fan blades to be volatilized by subsequent operation of the fan. The liquid volatile composition may continue to volatilize at a slower rate when the motor is stopped.

The liquid volatile composition may include a variety of materials, such as perfumes, insect repellents, insecticides, deodorants and/or odor neutralizers, and the like. The liquid volatile composition may be applied to the fan blades by the user, or the fan blades may pre-loaded with the liquid volatile composition at the time of purchase. A user may continue to add additional or different liquid volatile composition to the fan blades over time. A user may be able to wash the fan blades to apply a different liquid volatile composition to the fan blades. The fan blades may also be replaceable with new fan blades.

While the below description describes the volatile composition dispenser comprising a reservoir and a fan, both having various components, it is to be understood that the volatile composition dispenser is not limited to the construction and arrangement set forth in the following description or illustrated in the drawings. The volatile composition dispenser and fan blades of the present disclosure are applicable to other configurations or may be practiced or carried out in various ways. For example, the components of the fan may be configured as a single unit that is separable from the reservoir, or the only the fan blades may be separable from the reservoir, motor, and hub of the fan. Moreover, the fan and/or fan blades may be used with various devices for delivering a liquid volatile composition into the air.

Figure 1:
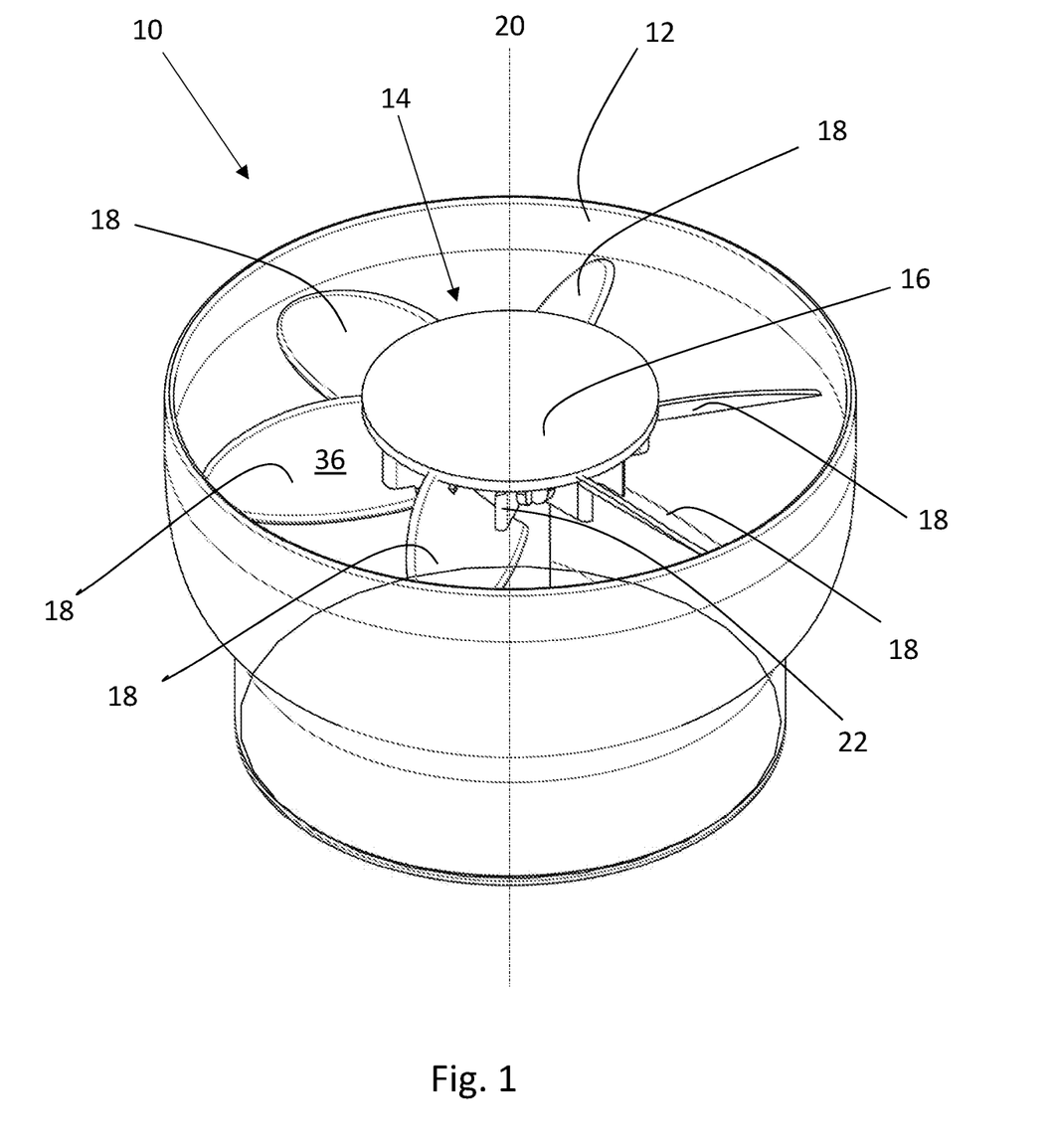
FIG. 1 is a perspective view of a volatile composition dispenser having a plurality of absorbent fan blades in an open configuration.
Figure 2:
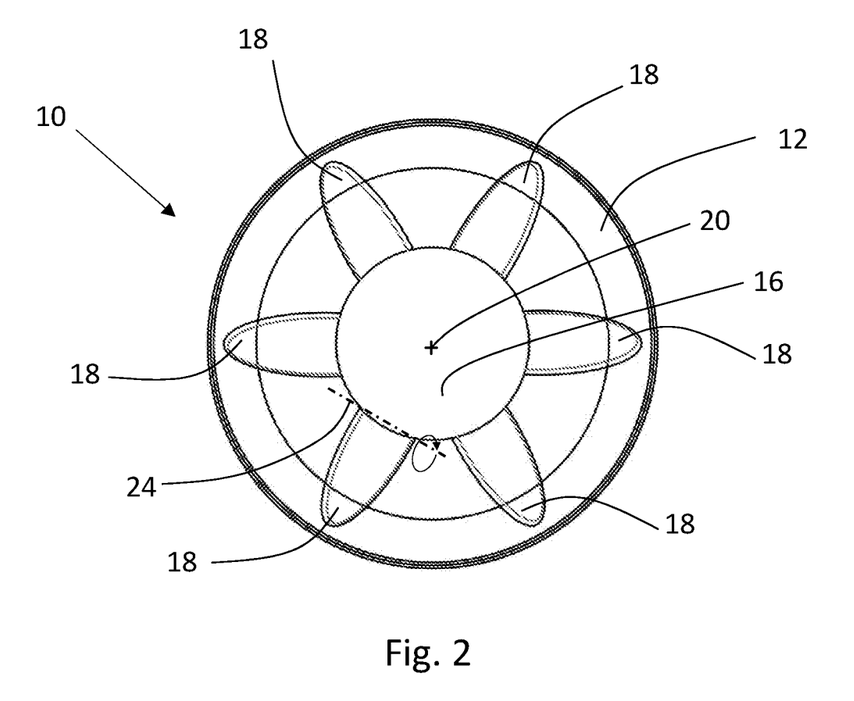
FIG. 2 is a top, plan view of the volatile composition dispenser of FIG. 1.
Figure 3:
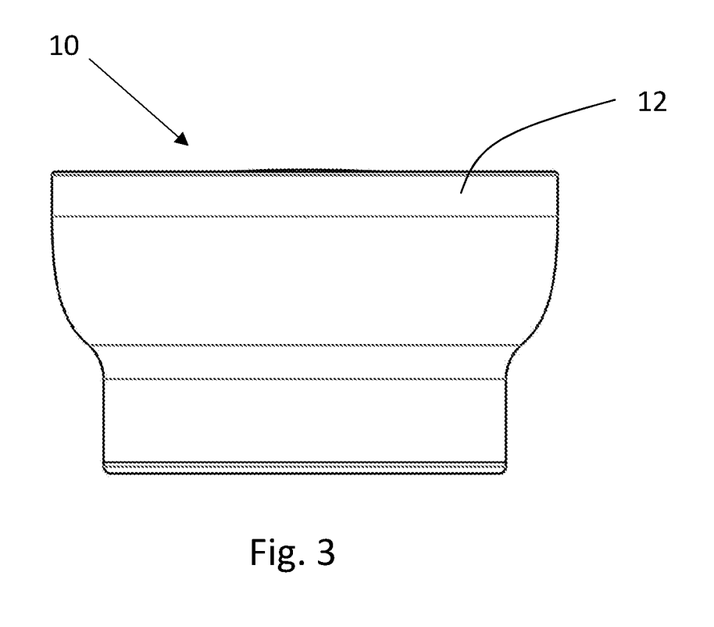
FIG. 3 is a side, elevation view of the volatile composition dispenser of FIG. 1.
Figure 4:
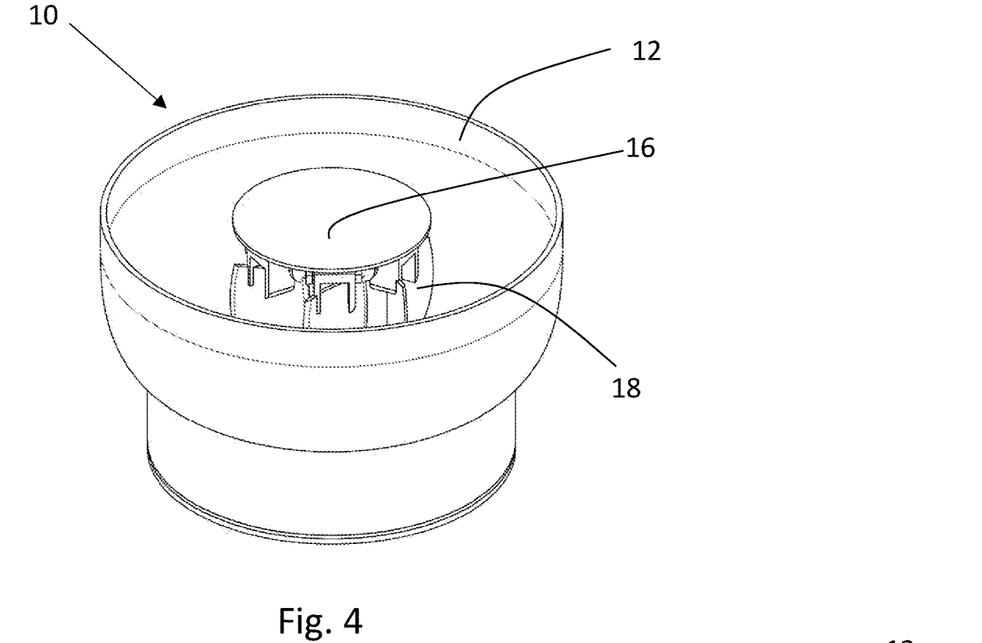
FIG. 4 is a perspective view of a volatile composition dispenser having a plurality of absorbent fan blades in a closed configuration.
Figure 5:
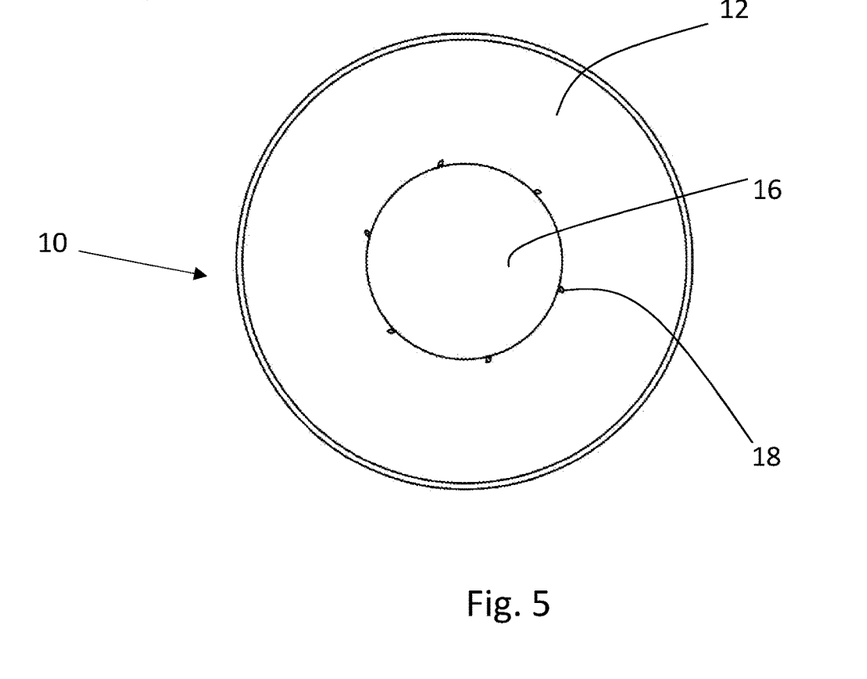
FIG. 5 is a top, plan view of the volatile composition dispenser of FIG. 4.

With reference to FIGS. 1-3, a volatile composition dispenser 10 includes a reservoir 12 and a fan 14 disposed at least partially in the reservoir 12. The fan 14 includes a motor, a hub 16 rotatably connecting and at least partially covering at least a portion of the motor, and one or more fan blades 18 connected with the hub 16. The hub 16 is configured to rotate about rotation axis 20. The fan blades 18 may be connected with the hub 16 at a connection 22. The fan blade(s) 18 is capable of pivoting about a pivot axis 24 from a closed configuration such, as shown in FIGS. 4 and 5 when the fan is turned OFF, to an open configuration, such as shown in FIGS. 1 and 2 when the fan 14 is turned ON. As will be discussed in more detail below, when the fan is turned ON, liquid volatile composition disposed on or absorbed into the fan blade(s) 18 is volatilized with the assistance of the air flow generated by the rotation of the hub 16.

The reservoir 12 may be configured in various different ways, including various shapes, colors, materials, etc. The centrifugal force imposed on the fan blades 18 may cause some of the liquid volatile composition to be released from the fan blade(s) 18 in the form of liquid droplets. The reservoir 12 functions to collect any liquid droplets of liquid volatile composition that are released from the fan blade(s) 18. The reservoir 12 may include a base 26 and one or more sidewalls 28 connected with and extending from the base 26 and terminating at an opening 32. The base 26 and sidewall (s) 28 may be integral or separate components that are joined together. The sidewall(s) 28 and/or the base 26 may slope inward toward the center of the base 26 to accumulate the liquid volatile composition droplets at or near the center of the base 26. When the fan blade(s) is in the closed configuration, the fan blade(s) 18 are in fluid communication with the liquid volatile composition in the reservoir, such that the fan blade(s) can reabsorb the liquid volatile composition accumulated in the base 26.

The opening 32 of the reservoir 12 may be configured in different shapes, such as circular, oval, square, square, rectangular, etc. The reservoir 12 may be a bowl or basin shape, such as shown in FIG. 1. The reservoir 12 may be composed of one or more materials, including plastic, glass, wood, the like, and combinations thereof. The material of the reservoir 12 in contact with the liquid volatile composition may be inert to the liquid volatile composition to be used with the volatile composition dispenser.

The fan 14 may be disposed at least partially within the reservoir 12 to collect the unvolatilized droplets of liquid volatile composition that are released from the fan blade(s) 18 and onto the reservoir 12. The fan 14 may be joined directly with the reservoir 12 or the fan 14 may be connected with an arm 30 extending from the reservoir 12. In a non-limiting example such as shown in FIG. 1, the fan 14 may be connected with arm 30 that extends from the center of the base 26 of the reservoir 12. Connecting the fan 14 to the arm 30 allows the fan 14 to be elevated away from the base 26, allowing the fan blade(s) 18 to hang down in the closed configuration, such as shown in FIG. 4 to absorb liquid volatile composition collected in the reservoir 12.

The fan 14 can be configured as an axial fan. The axial fan can comprise a hub 16 that is rotatably connected with the motor and at one or at least two fan blades 18 connected with and extending from the hub 16. A drive shaft of the motor can be operably engaged with the hub 16 such that rotation of the drive shaft by the motor rotates the rotatable hub and thereby rotates the fan blades 18 about the rotation axis 20. An electrical current can be provided to the axial motor via electrically conductive leads or terminal to rotate the draft shaft. Such rotation can cause a volume of air to be drawn into the reservoir 12 and out of the reservoir 12 through the fan blades 18. The fan 14 may comprise 2, 3, 4, 5, 6 or more fan blades 18.

Each fan blade 18 may be connected with the hub 16 at a connector 22. The fan blades 18 may be permanently or releasably connected with the hub 16 with the connector 22. The fan blades 18 may connect with the hub 16 in various ways. The connector 22 may be a mechanical connector, such as a hinge, clip, clamp, pin, fastener, snap, buckle, spring-loaded fastener, threaded fastener, hook-and-loop fastener, or the like, and combinations thereof. The connector 22 may also be a permanent or releasable adhesive, tape, the like, or combinations thereof. A separate connector 22 may join each fan blade 18 to the hub 16.

Figure 6:
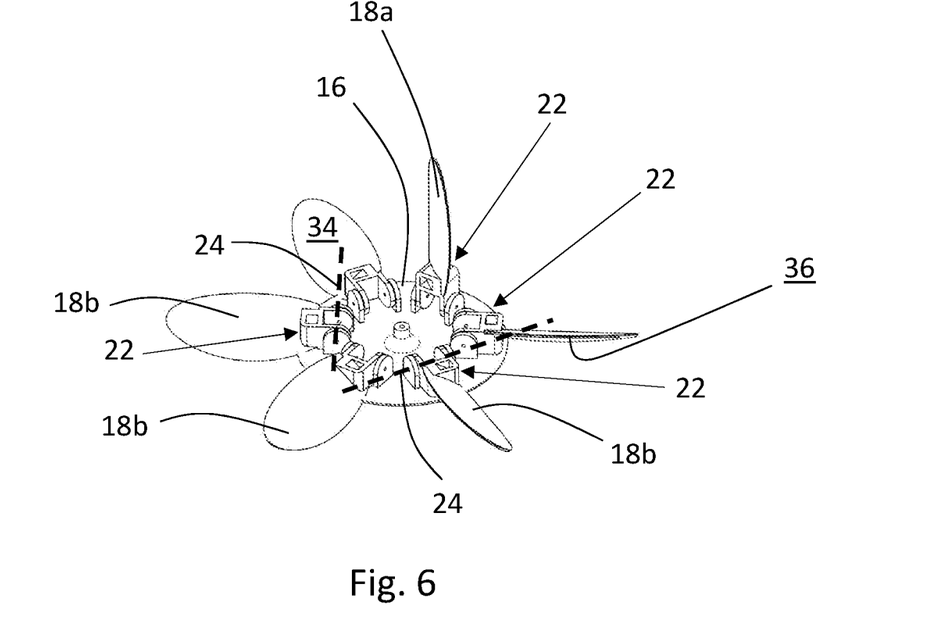
FIG. 6 is a perspective view of a hub, connectors, and fan blades of a volatile composition dispenser.

The connector 22 may define the pivot axis 24. As shown in FIGS. 1-2 and 6-7, the connector may be a mechanical hinge joint. The connectors 22 are joined with the underside of the hub 16. Each fan blade 18 may be connected with a separate connector 22. In the configuration shown in FIGS. 6 and 7, the pivot axis 24 is defined by the design of the connector 22. As illustrated in FIG. 6, the fan blade 18 pivots from the closed configuration, such as shown by fan blade 18*a*, to an open configuration, such as shown by fan blades 18*b*. The fan blades 18 may be movable relative to the connector 22 or may be fixed (permanently or temporarily) relative to the connector 22.

In a configuration where the connector 22 does not comprise a hinge or movable joint, such as adhesive, tape, hook-and-loop fastener, snap, or the like, the pivot axis 24 may be disposed adjacent to the connector 22. For example, if adhesive, tape, hook-and-loop fasteners, or the like are used as a connector 22 to join the fan blade(s) 18 to the hub 16, and the fan blade 18 is a flexible or semi-flexible material, a portion of the fan blade 18 adjacent to the connected portion of the fan blade may move freely relative to the hub 16. When the motor is OFF, the fan blade 18 may hang down, substantially parallel with the rotation axis 20. When the motor is ON, the fan blade 18 may be lifted by centrifugal force to a point of being substantially perpendicular to the rotation axis 20.

The connector 22 may be connected with the hub 16 in various ways. For example, the connector, or a portion thereof, may be permanently connected with the hub 16. In such a configuration, new fan blades 18 may be releasably connected with the connector 22. The connector 22 or a portion thereof may be releasably connectable with the hub 16 and/or the fan blade 18. The fan blade 18 may be pre-connected with the connector 22 or a user may have to manually connect the fan blade 18 with the connector 22.

The fan blades 18 may be comprised of an absorbent material. The absorbent material may be selected from the group consisting of: woven material, non-woven material, foam, or combinations thereof. The absorbent material of the fan blade 18 may be capable of absorbing the liquid volatile composition, and releasing at least the volatized portion of the liquid volatile composition. The absorbent material may also release liquid volatile composition in the form of droplets. An absorbent material may be selected based on the material's absorbency, pore structure, material, hydrophilicity or hydrophobicity, charge, etc.

The fan blades 18 may be configured in various different sizes, shapes, colors, and materials. Each fan blade 18 in the volatile composition dispenser 10 may be the same, or one or more of the fan blades 18 may be different from the rest of the fan blades 18. The fan blades 18 can be arcuate, straight, and/or can have curved, straight, and/or arcuate portions. Additionally, the fan blades 18 can have various cross-sectional shapes, such as leaf shaped, oval shaped, arcuate shaped, tapered shape an airfoil shape or a tapered shape, for example.

Figure 7:
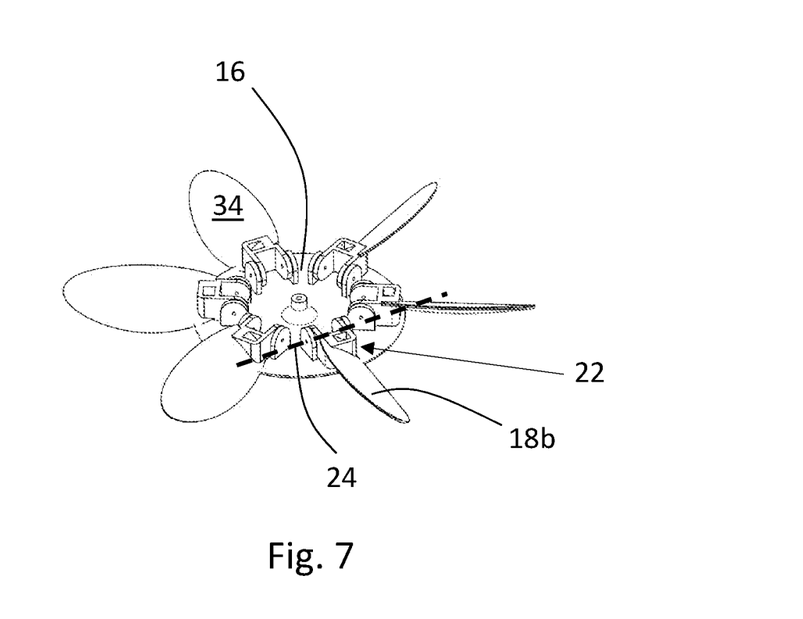
FIG. 7 is a perspective view of a hub, connectors, and fan blades of a volatile composition dispenser.

With reference to FIGS. 6 and 7, the fan blades 18 may comprise an inner surface 34 and an outer surface 36. The inner surface 34 may be the air receiving surface and the outer surface 36 may be the air releasing surface. The liquid volatile composition may absorb into the entirety of the fan blade 18 or the liquid volatile composition may be configured to absorb into portions of the fan blade 18.

The motor can be a Mabuchi RF-J20WA-5Z145 motor that rotates the drive shaft at about 6200 revolutions per minute when 0.7 VDC is supplied to the motor from a power source and rotates the driveshaft at about 9400 revolutions per minute when 1.0 VDC is supplied to the motor from the power source. The flow rate of the volume of air generated by the motor can be in the range of about 1.0 to about 8.0 mL/sec at about 0.7 VDC to about 6.0 to about 16.0 mL/sec at 1.0 VDC. By supplying various voltage levels to the motor, the rotational speed of the drive shaft and the resultant flow rate of the volume of air can be varied. Any other suitable motor can also be used with the fan, such as a Sunon UB393-10 fan, for example. Additionally, a controller can supply the motor with voltage using any suitable technique known to those of skill in the art. A pulse width modulation technique can be used to provide voltage to the motor over a specified range, such as about 0.7 VDC to about 1.0 VDC, for example. Additional circuitry or components, such as an analog-to-digital converter, can be used to compensate for various factors, such as the power source voltage and the ambient temperature, for example. In order to isolate or limit vibration due to the rotation of the drive shaft and/or the hub 16, vibration suppression devices or techniques can be used, such as silicon or thermoplastic elastomeric fan supports.

Suitable fans for the present invention include a 30×30×6 mm MagLev Motor Fan (Model MC30060V1-000U-A99), supplied by Sunon Wealth Electric Machine Industry Co., Ltd of Taiwan; and fan model RF-330TK 07800, supplied by Mabuchi Motor. Another suitable fan for the present invention may have the following specifications:

Dimension: 120×120×25 mm
Fan Speed: 800-1500 rpm+250 RPM
Max Airflow: 66.55 CFM
Max Air Pressure: 1.42 mm $H_2O$
Bearing Type: Sleeve
Power: 5V The fan 14 is powered by a power source which may comprise a AC/DC outlet, a battery, such as a AA battery, a AAA battery, a 9-volt battery, rechargeable battery, and/or other suitable battery. A solar power source, such as a solar cell, for example, can be used to power the volatile composition dispenser 10. The solar cell (i.e., a photovoltaic cell) can be positioned on an outer portion of the volatile composition dispenser 10 or in communication with the motor of the fan 14, such that the solar cell can receive light that can be transformed into energy to power the motor of the fan 14 and any other electrical components.

The diameter of the rotatable hub 84 can be about 8 mm to about 20 mm, for example, although other dimensions could be possible.

The fan 14 may produce air speeds in the range of about 5 feet per minute to 400 feet per minute or alternatively from about 50 feet per minute to 250 feet per minute; although others air speeds could be possible.

The duration of activation of the fan 14 or the flow rate of the volume of air provided by the fan 14 can be increased to provide a higher intensity of volatile composition expulsion from the volatile composition dispenser 10. The fan 14 can operate continuously or have intermittent operation. The fan 14 may toggle on and off for a duty cycle of about 5% to about 50%, or from about 8% to about 20%. By providing a period of time between consecutive activations of the fan, a user is more likely to notice a scent of the volatile composition again and avoid habituation.

Table 1 provides exemplary activation or toggling patterns of the fan 14. As will be appreciated by those of skill in the art, a continuous operation of the fan and/or different pulsing frequencies and/or different air flow rates can be used to deliver different scent experiences.

TABLE 1

| Example Duty Cycles | Fan Active Time Period | Fan Inactive Time Period |
| --- | --- | --- |
| High (50% duty cycle) (may be more efficient for volatile composition release but may use more power due to frequent activation and deactivation of the fan 80) | 10 sec | 10 sec |
| High (50% duty cycle) (may be less efficient for volatile composition release but may not use as much power due to activation and deactivation of the fan 80) | 30 sec | 30 sec |
| High (50% duty cycle) (may be less efficient for volatile composition release but may not use as much power due to activation and deactivation of the fan 80) | 1 min | 1 min |
| High (50% duty cycle) (may be less efficient for volatile composition release but may not use as much power due to activation and deactivation of the fan 80) | 10 min | 10 min |
| Medium (20% duty cycle) | 10 sec | 40 sec |
| Medium (20% duty cycle) | 30 sec | 120 sec |
| Medium (20% duty cycle) | 90 sec | 360 sec |
| Medium (20% duty cycle) | 1 min | 4 min |
| Medium (20% duty cycle) | 3 min | 12 min |
| Medium (20% duty cycle) | 10 min | 40 min |
| Medium-Low (12.5% Duty Cycle) | 10 sec | 70 sec |
| Medium-Low (12.5% Duty Cycle) | 30 sec | 210 sec |
| Medium-Low (12.5% Duty Cycle) | 1 min | 7 min |
| Medium-Low (12.5% Duty Cycle) | 3 min | 21 min |
| Low (10% duty cycle) | 10 sec | 90 sec |
| Low (10% duty cycle) | 20 sec | 180 sec |
| Low (10% duty cycle) | 1 min | 9 min |
| Low (10% duty cycle) | 4 min | 36 min |
| Low (10% duty cycle) | 10 min | 90 min |
| Very Low (8% duty cycle) | 10 sec | 120 sec |
| Very Low (8% duty cycle) | 30 sec | 360 sec |
| Very Low (8% duty cycle) | 1 min | 12 min |
| Very Low (8% duty cycle) | 3 min | 36 min |
| Ultra Low (5% duty cycle) | 5 sec | 95 sec |
| Ultra Low (5% duty cycle) | 10 sec | 190 sec |
| Ultra Low (5% duty cycle) | 20 sec | 380 sec |
| Ultra Low (5% duty cycle) | 1 min | 19 min |

The evaporation rate of a liquid volatile composition from the volatile composition dispenser 10 can be about 5 mg/hr to about 75 mg/hr, or about 10 mg/hr to about 75 mg/hr, Or about 15 mg/hr to about 70 mg/hr, or about 25 mg/hr to about 70 mg/hr, or about 25 mg/hr to about 60 mg/hr, or about 25 mg/hr to about 40 mg/hr.

It is contemplated that evaporation assistance elements can be utilized to achieve the evaporation rate of a volatile composition from the volatile composition dispenser. The evaporation assistance element may include a heating element to heat the liquid volatile composition, a chemical constituent to speed evaporation or release rates, or synergistic combinations thereof.

A controller may be positioned in electrical communication with the fan 14, such that the controller can instruct the fan 14 when to activate and which speed to rotate. The controller can be any suitable type of controller, such as a microcontroller, for example. The controller can be a Texas Instruments MSP430F2132 controller. The controller can comprise one or more user input buttons or switches configured to provide an input signal to the controller when depressed by a user, such that the controller can send corresponding output signals to the fan 14 and/or the user feedback module, for example. The various user input buttons or switches can comprise a power ON/OFF switch configured to power on or power off the volatile composition dispenser 10 and/or at least one volatile composition dose amount button configured to allow the user to adjust the amount of volatile composition dispensed by the volatile composition dispenser 10. As will be appreciated, the input buttons or switches can be any combination of buttons and/or switches, such as push buttons, sliders, dials, knobs, for example.

The volatile composition dispenser 10 can comprise a sensor, such as a visible indicator, a light source, and/or an audible alert, configured to provide feedback to the user regarding the status of the volatile composition dispenser 10. In one embodiment, the sensor can be used to alert the user of a property of the volatile composition dispenser 10. In such embodiments, the feedback can be visual and/or audible and can indicate to the user, among other things, whether the volatile composition dispenser 10 is powered on, what volatile composition dosing amount is being dispensed, the power level of the power source, the amount, type, or level of the liquid volatile composition within the reservoir, and/or any other suitable feedback helpful or beneficial to the user. The sensor can comprise one or more one indicators, such as a plurality of light sources, for example, electrically coupled to the controller and/or to the power source, and a translucent portion in the reservoir, such that the one or more indicators can be viewed by the user though the volatile composition dispenser 10. One or more indicators can be oriented in any suitable fashion such that various lights of the one or more indicators can emit visible light through the translucent portion of the volatile composition dispenser 10, depending on what type of feedback is being provided to the user. The translucent portion of the volatile composition dispenser 10 can comprise any suitable shape and the one or more indicators can be arranged in a similar shape so that as one indicator, such as a light source, for example, is powered or unpowered, the user is provided with a first feedback and, as two or more light sources are powered or unpowered, the user is provided with at least a second feedback and so forth. At least one button is at least partially translucent allowing for one or more indicators to be viewable through the button.

The liquid volatile composition may comprise various materials. For example, the liquid volatile composition may include one or more perfumes and/or insect repellants. The liquid volatile composition may include one or more diluents, solvents, aqueous carriers, and the like. The liquid volatile composition may include at least 30 wt. %, alternatively at least 40 wt. %, alternatively at least 50 wt. %, alternatively at least 60 wt. %, alternatively at least 75 wt. % of perfume raw materials and/or insect repellants, by total weight of the liquid volatile composition. The liquid volatile composition may include, in addition to perfume or as an alternative to perfume, malodor counteractants, odor insecticides, and the like.

The perfumes may include one or more of the following perfume raw materials. As used herein, a "perfume raw material" refers to one or more of the following ingredients: fragrant essential oils; aroma compounds; pro-perfumes; materials supplied with the fragrant essential oils, aroma compounds, and/or pro-perfumes, including stabilizers, diluents, processing agents, and contaminants; and any material that commonly accompanies fragrant essential oils, aroma compounds, and/or pro-perfumes.

Figure 8:
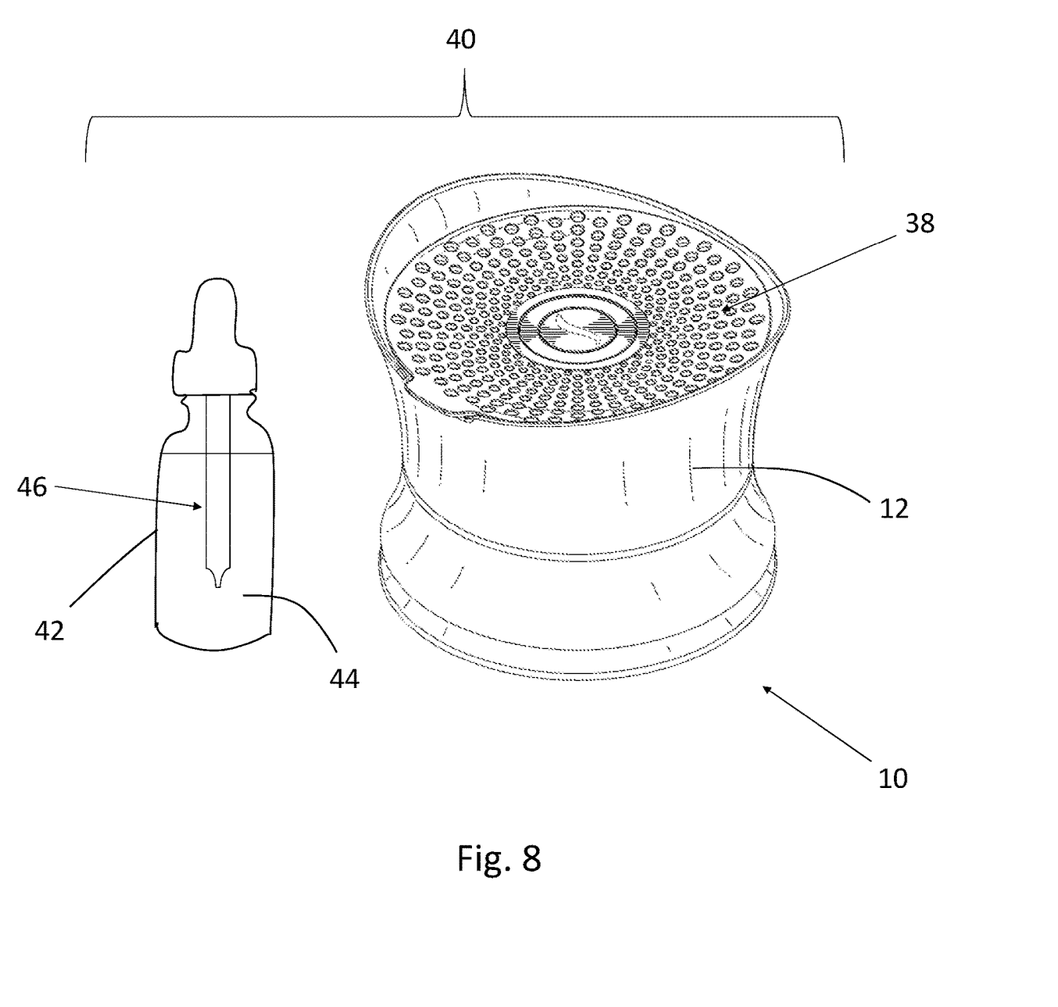
FIG. 8 is a schematic, perspective view of a kit having a volatile composition dispenser and a separate container of liquid volatile composition.

With reference to FIG. 8, the volatile composition dispenser 10 may include other components, such as a vent 38 for at least partially covering the opening of the reservoir 12. The vent 38 may temporarily limit access to the fan blades 18, keeping a user from being able to contact the fan 14 or fan blades 18 while the motor is ON.

With continuing reference to FIG. 8, the volatile composition dispenser 10 may be available as a kit 40 comprising a volatile composition dispenser 10 and additional, replaceable fan blades and/or a separate container 42 of liquid volatile composition 44. The fan blades may be pre-loaded with the liquid volatile composition, or the user may load the separate liquid volatile composition onto the fan blades before use. Additional fan blades, either the absorbent material alone or the absorbent material pre-loaded with the liquid volatile composition may also be available for a user to purchase as a refill. A container 42 of liquid volatile composition may be configured in various ways and may include a dispensing element, such as a tincture container with a dropper 46 such as shown in FIG. 8. The dropper 46 may be used to dispense the liquid volatile composition 44 onto the fan blades 18.

In operation, the volatile composition dispenser is connected with a power source, either external or with the use of batteries. To turn on the fan, power to the motor is turned ON. The motor may run continuously until turned off, or may be programmed to turn ON and OFF intermittently through a program. When the motor is ON, the hub rotates about the rotation axis, causing the fan blade(s) to also rotate about the rotation axis. The centrifugal force acting on the fan blade(s) causes the fan blade(s) to move from a closed configuration to an open configuration. As the fan blades rotate in the open configuration, a portion of the liquid volatile composition disposed on the fan blades volatilizes into the air. A portion of the liquid volatile composition may be forced from the fan blade(s) in the form of liquid droplets. Any liquid droplets released from the fan blade(s) may be caught by the reservoir and may be funneled to the base of the reservoir. When the motor is OFF, the fan blades return to the closed configuration. When in the closed configuration, the fan blades may be in fluid communication with any liquid volatile composition in the base of the reservoir. If liquid volatile composition is present in the base of the reservoir, the fan blade(s) can absorb the liquid volatile composition and be volatilized the subsequent operation of the fan motor.

The method may include a user applying or reapplying liquid volatile composition to the fan blade(s). The method may also include a user removing one or more of the fan blades and connecting one or more new fan blades with the hub.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A volatile composition dispenser comprising:
   a reservoir;
   a fan disposed at least partially in the reservoir, wherein the fan comprises a motor, a hub rotatably connected to the motor about a rotation axis, a fan blade connected with the hub, wherein the fan blade is movable relative to the hub about a pivot axis, wherein the pivot axis is perpendicular or substantially perpendicular to the rotation axis, wherein the fan blade comprises an absorbent material.

2. The volatile composition dispenser of claim 1 further comprising a connector that joins the fan blade with the hub.

3. The volatile composition dispenser of claim 2, wherein the connector is selected from the group consisting of: hinge, clip, clamp, pin, fastener, snap, buckle, spring-loaded fastener, threaded fastener, hook-and-loop fastener, permanent or releasable adhesive, tape, and combinations thereof.

4. The volatile composition dispenser of claim 1, wherein the absorbent material is selected from the group consisting of: woven material, non-woven material, foam, or combinations thereof.

5. The volatile composition dispenser of claim 1, wherein the fan comprises a plurality of fan blades connected with the hub.

6. The volatile composition dispenser of claim 1, wherein the fan blade is releasably connectable with the hub.

7. The volatile composition dispenser of claim 1, wherein the fan blade comprises a liquid volatile composition, wherein the liquid volatile composition comprises a material selected from the group consisting of: a perfume, an insect repellant, a deodorizer, a malodor counteractant, and combinations thereof.

8. The volatile composition dispenser of claim 1, wherein the fan blade is configured such that when the motor is on, centrifugal force causes the fan blade to move from a closed configuration to an open configuration, wherein the angle between the closed configuration and the open configuration is about 90 degrees.

9. A kit comprising the volatile composition dispenser of claim 1 and a container comprising a liquid volatile composition.

10. A volatile composition dispenser comprising:
a reservoir;
a fan disposed at least partially in the reservoir, wherein the fan comprises a motor, a hub rotatably connected to the motor about a rotation axis, a fan blade connected with the hub, wherein the fan blade is movable about a pivot axis relative to the hub, wherein the fan blade is movable from a closed configuration to an open configuration, wherein an angle between the closed configuration and the open configuration is about 90 degrees, and wherein the fan blade comprises an absorbent material.

11. The volatile composition dispenser of claim 10 further comprising a connector that joins the fan blade with the hub, wherein the connector is selected from the group consisting of: hinge, clip, clamp, pin, fastener, snap, buckle, spring-loaded fastener, threaded fastener, hook-and-loop fastener, permanent or releasable adhesive, tape, and combinations thereof.

12. The volatile composition dispenser of claim 10 further comprising a vent at least partially enclosing the reservoir.

13. The volatile composition dispenser of claim 10, wherein the absorbent material is selected from the group consisting of: woven material, non-woven material, foam, or combinations thereof.

14. The volatile composition dispenser of claim 10, wherein the fan comprises a plurality of fan blades connected with the hub.

15. The volatile composition dispenser of claim 10, wherein the fan blade is releasably connectable with the hub.

* * * * *